United States Patent
Beier et al.

(10) Patent No.: US 11,311,479 B2
(45) Date of Patent: Apr. 26, 2022

(54) NANOPARTICLES COMPRISING TACROLIMUS

(71) Applicant: leon-nanodrugs GmbH, Munich (DE)

(72) Inventors: Wolfgang Beier, Munich (DE); Elke Horstkotte, Munich (DE)

(73) Assignee: LEON-NANODRUGS GMBH, Munich (DE)

( * ) Notice: Subject to any disclaimer, the term of this patent is extended or adjusted under 35 U.S.C. 154(b) by 221 days.

(21) Appl. No.: 16/702,649

(22) Filed: Dec. 4, 2019

(65) Prior Publication Data

US 2020/0170934 A1 Jun. 4, 2020

(30) Foreign Application Priority Data

Dec. 4, 2018 (DE) .................... 10 2018 130 848.5

(51) Int. Cl.
*A61K 9/00* (2006.01)
*A61K 9/51* (2006.01)
*A61K 31/436* (2006.01)

(52) U.S. Cl.
CPC ............ *A61K 9/006* (2013.01); *A61K 9/5138* (2013.01); *A61K 9/5146* (2013.01); *A61K 9/5161* (2013.01); *A61K 9/5192* (2013.01); *A61K 31/436* (2013.01)

(58) Field of Classification Search
None
See application file for complete search history.

(56) References Cited

FOREIGN PATENT DOCUMENTS

WO 2006066063 A1 6/2006
WO 2017129177 A1 8/2017

OTHER PUBLICATIONS

Ruihua Wang, Longnian Li, Bing Wang, Tangde Zhang and Ledong Sun"FK506-loaded solid lipid nanoparticles: Preparation, characterization and in vitro transdermal drug delivery", African Journal of Pharmacy and Pharmacology, vol. 6, No. 12, Mar. 29, 2012 (Mar. 29, 2012), XP055748514, DOI: 10.5897/AJPP11.831.
Taste-masked tacrolimus-phospholipid nanodispersions: dissolution enhancement, taste masking and reduced gastric complications, Ahmed S. Zidan; Pharmaceutical Development and Technology, vol. 22, No. 2, Feb. 17, 2017 (Feb. 17, 2017), pp. 173-183, XP055667592, US; ISSN: 1083-7450; DOI: 10.3109/10837450. 2016.1138131.

*Primary Examiner* — Nannette Holloman
(74) *Attorney, Agent, or Firm* — Shumaker, Loop & Kendrick, LLP; James D. Miller

(57) ABSTRACT

Nanoparticles including tacrolimus, and a method for providing nanoparticles including tacrolimus as well as to nanoparticles including tacrolimus that are obtainable by said method. Also relates to the nanoparticles including tacrolimus for use as a medicament. Further relates to a mucoadhesive buccal film containing the nanoparticles including tacrolimus and the mucoadhesive buccal film for use as a medicament, especially in pediatric patients.

9 Claims, No Drawings

NANOPARTICLES COMPRISING TACROLIMUS

CROSS-REFERENCE TO RELATED APPLICATION

This patent application is a United States Utility Patent Application which claims priority to German Patent Application Serial No. DE 10 2018 130 848.5 filed Dec. 4, 2018, the entire disclosure of which is hereby incorporated herein by reference.

FIELD OF THE INVENTION

The present invention is directed to nanoparticles comprising tacrolimus, a method for providing nanoparticles comprising tacrolimus as well as to nanoparticles comprising tacrolimus obtainable by said method. The invention is further directed to the nanoparticles comprising tacrolimus for use as a medicament, in particular for use as a medicament in pediatrics, more particular in the treatment of solid organ transplant rejection especially in pediatric patients. The invention is further directed to a mucoadhesive buccal film containing said nanoparticles comprising tacrolimus and said mucoadhesive buccal film for use as a medicament, particularly in pediatrics, more particular in the treatment of solid organ transplant rejection especially in pediatric patients.

BACKGROUND OF THE INVENTION

Tacrolimus, also known as fujimycin or FK506, is an immunosuppressive drug used mainly after allogeneic organ transplant to lower the risk of organ rejection. It achieves this by inhibiting the production of interleukin-2, a molecule that promotes the development and proliferation of T cells, which are vital to the body's learned (or adaptive) immune response.

Chemically it is a 23-membered macrolide lactone that was first discovered in the fermentation broth of a soil sample that contained the bacterium *Streptomyces tsukubaensis*. Despite the fact that oral formulations of tacrolimus have been on the market for more than two decades, there is not yet an optimal pediatric formulation available that allows easy and patient convenient application.

Tacrolimus is a lipophilic compound with a molecular weight of about 822 Da, which is practically insoluble in water (0.004 mg/ml), resulting in low bioavailability.

A further factor for the reduced and rather unpredictable bioavailability is the extensive first pass metabolism of tacrolimus by CYP3A4/5 in gut and liver, P-glycoprotein mediated drug efflux, genetic variations, influence of food intake and concomitant medications.

This requires sophisticated formulations in order to achieve an acceptable bioavailability of the drug.

SUMMARY OF THE INVENTION

Hence, it was the objective of the present invention to provide tacrolimus in a form with increase water-solubility as well as a method for providing tacrolimus in such a form. It was further the objective of the present invention to provide a therapeutic system for the delivery of tacrolimus to a patient that avoids or by-passes the first-pass metabolism by buccal absorption of tacrolimus and thus translates into a higher and more predictable bioavailability. Further, the therapeutic system for delivering tacrolimus shall protect the drug from degradation due to pH and digestive enzymes of the gastrointestinal tract, it shall provide a rapid onset of action relative to the buccal route and it shall be an easy and convenient way of drug administration. It shall further avoid hurdles related to drug administration via nasogastric tube and shall be flexible in physical shape, state, size and surface. Moreover, the therapeutic system shall allow an accurate dosing as well as offering the possibility of masking the taste of tacrolimus.

These objectives have been solved by nanoparticles according to claim 1, that is by nanoparticles comprising tacrolimus or a salt thereof, wherein the nanoparticles have a particle size of about 10 to about 400 nm. The inventors have surprisingly found that such nanoparticles in the nanometer range exhibit a significant decrease in dissolution time as well as an increase in the saturation solubility.

Such nanoparticles can be provided using the method according to claim 5, that is by using a method for producing nanoparticles containing tacrolimus or a salt thereof comprising the steps of:
   a) providing a solution of tacrolimus or a salt thereof in an organic solvent;
   b) providing a liquid non-solvent for tacrolimus or a salt thereof, preferably water;
   c) precipitating nanoparticles containing tacrolimus or a salt thereof by colliding a stream of the organic solvent from a) with a stream of the non-solvent from b); and
   d) isolating the nanoparticles, wherein the nanoparticles have a size of from 10 to 400 nm, and preferably a polydispersity index of ≤about 0.4.

Moreover, the inventors have identified a mucoadhesive buccal film according to claim 15, in particular an mucoadhesive buccal film comprising at least one matrix layer containing the aforementioned nanoparticles comprising tacrolimus or a salt thereof and at least one polymer as a therapeutic system for delivering tacrolimus to a patient. Such a mucoadhesive buccal film is in particular suitable for delivering tacrolimus to a pediatric patient, i.e. to a child.

DETAILED DESCRIPTION OF THE INVENTION

Firstly, the invention relates to nanoparticles comprising tacrolimus or a salt thereof, wherein the nanoparticles have a particle size of about 10 to about 400 nm, preferably of about 100 to about 200 nm.

Such nanoparticles have the advantage that they exhibit a significant decrease in dissolution time as well as an increase in the saturation solubility compared to the single molecules.

The nanoparticles according to the invention are further preferably characterized in that the nanoparticles have a polydispersity index of about ≤0.4, preferably of about ≤0.2.

Their particle size is defined as their diameter determined by a suitable process, e.g. using Dynamic Light Scattering (DLS) (e.g. using a Malvern Zetasizer ZS90 from Malvern Instruments Ltd.). DLS measures Brownian motion and relates this to the size of the particles. Brownian motion is the random movement of particles due to the bombardment by the solvent molecules that surround them. The larger the particle or molecule, the slower the Brownian motion will be. Smaller particles are "kicked" further by the solvent molecules and move more rapidly. An accurately known temperature is necessary for DLS because knowledge of the viscosity is required (because the viscosity of a liquid is related to its temperature). In the present measurement a temperature of 25° C. is used. This temperature is kept constant during the measurement. The velocity of the Brownian motion is defined by the translational diffusion coefficient (D). The size of a particle is calculated from the translational diffusion coefficient by using the Stokes-Einstein equation $$d(H) = \frac{kT}{3\pi\eta D},$$

wherein d(H) is the hydrodynamic diameter, D is the translational diffusion coefficient, k is the Boltzmann's constant, T is the absolute temperature, and ri is the viscosity. The diameter that is obtained by the Stokes-Einstein equation is the diameter of a sphere that has the same translational diffusion coefficient as the particle. The particle translational diffusion coefficient will depend not only on the size of the particle "core", but also on any surface structure that will affect the diffusion speed, as well as the concentration and type of ions in the medium. Malvern Zetasizer series measure the velocity at which the particles diffuse due to Brownian motion by determining the rate at which the intensity of scattered light fluctuates when detected using a suitable optical arrangement. In the Zetasizer Nano ZS90 series, the detector position is 90°. The z-average diameter, together with the polydispersity index (PDI), are calculated from the cumulants analysis of the DLS measured intensity autocorrelation function as defined in ISO 22412:2008. PDI is a dimensionless estimate of the width of the particle size distribution, scaled from 0 to 1. According to Malvern Instruments, samples with PDI≤0.4 are considered to be monodisperse.

The polydispersity index (PDI) is a parameter to define the particle size distribution of the nanoparticles obtained from dynamic light scattering (DSL) measurements. As mentioned above, the PDI might be measured using a Malvern Zetasizer according to the manufacturer's instructions. The smaller the PDI value is, the lower the width of particle size distribution. Generally, the polydispersity index PDI is used as measure of the width of the particle size distribution. Thus, particles or particles in suspensions may be generally divided into monodisperse and polydisperse entities. For monodisperse, e.g. homogenous suspensions/particles, a tight particle size distribution is given. For polydisperse suspensions/particles, particle sizes vary considerably. Monodisperse particles are preferred.

Particle size, as well as the PDI are important factors affecting the dissolution rate of particular substances, e.g. pharmaceutical active ingredients. Thus, comparison of dissolution of two nanoparticular populations of one active pharmaceutical ingredient with comparable mean particle sizes but significantly differing PDI might result in significant change in dissolution behavior of those nanoparticles, with slower dissolution for the nanoparticles with higher PDI and faster dissolution for the nanoparticles with lower PDI. Thus, PDI might affect, beside particle size, the quality of nanoparticles.

The nanoparticles according to the present invention are further preferably characterized in that the nanoparticles further comprise at least one stabilizing agent.

The stabilizing agent has the function to stabilize the nanoparticles according to the present invention, especially in a pharmaceutical composition comprising the nanoparticles according to the present invention.

The stabilizing agent is preferably adsorbed on the surface of the nanoparticles, which in turn improves the stability of the nanoparticles.

The at least one stabilizing agent is not particularly limited but can comprise any suitable and pharmaceutically acceptable polymer, that is known to the skilled artist for such purpose. The stabilizing agent can be added either in the solvent or in the non-solvent. Preferably, the at least one stabilizing agent comprises polyvinyl pyrrolidone (PVP), vinylpyrrolidone-/vinylacetate-copolymer, polyethylenglycol and/or a cellulose derivative such as hydroxypropylmethyl cellulose (HPMC), hydroxypropylmethyl cellulose phthalate (HPMCP), hydroxypropylmethyl cellulose acetate succinate (HPMCAS), hydroxypropyl cellulose (HPC), and/or carboxymethyl cellulose (CMC).

The nanoparticles according to the present invention are further preferably characterized in that they further comprise at least a surfactant (which is an amphiphilic agent). Preferably the surfactant comprises sodium dodecyl sulfate (SDS), polysorbates, amphiphilic triblock copolymers such as polaxamers, amphiphilic diblock copolymers with a hydrophilic (e.g. PEG) and a hydrophobic block consisting e.g. of polystyrene (PS), poly-☐-caproloactone (PCL), polylactide (PLA), or poly(lactic-co-glycolic acid) (PLGA), D-alpha-Tocopheryl Polyethylenglycol 1000 Succinat (TPGS), deoxycholic acid or a salt thereof, phosphatidylcholine, and/or chitosan.

In a very preferred embodiment, the nanoparticles comprise at least a stabilizing agent and at least a surfactant.

In a further aspect, the present invention is directed to a method for producing nanoparticles containing tacrolimus or a salt thereof, wherein the method comprises the steps of:
 a) providing a solution of tacrolimus or a salt thereof in an organic solvent;
 b) providing a liquid non-solvent for tacrolimus or a salt thereof, preferably water;
 c) precipitating nanoparticles containing tacrolimus or a salt thereof by colliding a stream of the organic solvent from a) with a stream of the non-solvent from b); and
 d) isolating the nanoparticles, wherein the nanoparticles have a size of from 10 to 400 nm, and preferably a polydispersity index of about 0.4.

A solvent is any kind of fluid substance, which is capable of dissolving tacrolimus.

The term "non-solvent" according to the present invention describes any fluid substance which is capable of precipitating tacrolimus containing nanoparticles by colliding a fluid stream of it with a fluid stream of the fluid mixture. Therefore, a "non-solvent" in the meaning of the present invention should not be interpreted narrowly, for example as a substance in which tacrolimus is insoluble. Preferably, the non-solvent cannot dissolve more than 1 mg/ml of tacrolimus.

The above described method for producing nanoparticles containing tacrolimus or a salt thereof is preferably carried out in a microjet reactor.

The term "microjet reactor" includes all the geometries that are defined in WO2017129177 A1. The contents of this patent application is incorporated herein by reference. WO2017129177 A1 provides for a system for the initiation of chemical or physical processes including at least two liquid media to be injected by means of pumps, preferably high-pressure pumps, into a reactor chamber enclosed by a reactor housing and on to a shared collision point, each medium being injected through one nozzle. Through an opening in the reactor chamber, a gas, an evaporating liquid, a cooling liquid or a cooling gas, is introduced so as to maintain the gas atmosphere in the reactor interior, notably in the collision point of the liquid jets, and to cool the resulting products. The resulting products and excess gas are removed from the reactor housing via a further opening by positive pressure on the gas input side or negative pressure on the product and gas discharge side. By diffusion of the solvent into non-solvent nanoparticles are formed with very defined particle size and particle size distribution.

The methods of the present invention thus preferably includes controlled solvent/non-solvent precipitation, wherein solvent and non-solvent streams collide as impinging jets with a high velocity of about 1 m/sec to about 100 m/sec, preferably about 50 m/sec. Thereby, the Reynold number is preferably higher than about 500. It is noted that the above indicated velocity is the velocity of each of the colliding streams, i.e., both the fluid stream of the fluid mixture and the fluid stream of the non-solvent have this velocity.

The solvent and the non-solvent preferably are sprayed through nozzles usually smaller than about 1000 m (for example smaller than about 500 m or about 300 m) with pressures of more than about 1 bar. Pressures of more than about 10 bars and even more than about 50 bar are suitable as well. The pressure may be regulated by pressure regulators.

The two streams collide in a reactor, where a very rapid mixing takes place. Mixing times usually are below about 1 millisecond, preferably below about 0.5 milliseconds, and even more preferably under about 0.1 millisecond. The flow rates of solvent and non-solvent streams may reach more than about 600 1/hour. Thus, the two impinging jets (or streams) collide in the reactor, where precipitation takes place forming disc like structures depending on the reactor geometry.

The method according to the present invention is further preferably characterized in that the solvent comprises ethanol, methanol, acetone, tetrahydrofuran, acetic acid, acetonitrile, anisole, 1-Butanol, 2-Butanol, butyl acetate, chloroform, cyclohexan, 1,1,-diethoxypropane, 1,1-dimethoxymethane, 1,2-dimethoxyethane, 1,4-dioxane, 2,2-dimethoxypropane, dichlormethan, diethyl ether, di-isopropyl ether, dimethyl sulfoxide, dimethylformamide, dimethylformamide, 2-ethoxyethanol, ethyl acetate, ethyl formate, ethylenglycol (1,2-Ethandiol), formic acid, heptane, hexane, isobutyl acetate, isopropyl acetate, 2-methoxyethanol, 2-methyl-1-propanol, 3-methyl-1-butanol, 1-methyl-2-pyrrolidone, methyl acetate, methyl t-butyl ether, methylbuylketon, methylcyclohexane, methylethyl ketone (MEK), methylisobutyl ketone, methylisopropyl ketone, methylthetrahydrofuran, n-methylpyrrolidone, 1-pentanol, 1-propanol, 2-propanol, pentane, petroleum ether, propyl acetate, pyridine, sulfolane, t-butyl alcohol, 2,2,4-trimethylpentan (i-Octan), toluol, trichloroacetic acid, trichloroethylene, trifluroacetic acid and/or xylol.

Preferably, tacrolimus is dissolved in the solvent in a concentration of about 10 mg/ml to about 500 mg/ml.

The method according to the invention is further preferably characterized in that the solvent or the non-solvent further comprises at least one stabilizing agent, preferably polyvinyl pyrrolidone, vinylpyrrolidone-/vinylacetate-copolymer, polyethylenglycol, and/or a cellulose derivative such as hydroxypropylmethyl cellulose (HPMC), hydroxypropylmethyl cellulose phthalate (HPMCP), hydroxypropylmethyl cellulose acetate succinate (HPMCAS), hydroxypropyl cellulose (HPC), and/or carboxymethyl cellulose (CMC).

The stabilizing agent might preferably be combined with at least one surfactant, e.g. sodium dodecyl sulfate (SDS), polysorbates, amphiphilic triblock copolymers such as polaxamers, amphiphilic diblock copolymers with a hydrophilic (e.g. PEG) and a hydrophobic blocks consisting e.g. of polystyrene (PS), poly-□-caproloactone (PCL), polylactide (PLA), or poly(lactic-co-glycolic acid) (PLGA), D-alpha-Tocopheryl Polyethylenglycol 1000 Succinat (TPGS), deoxycholic acid or a salt thereof, phosphatidylcholine and/or chitosan. The surfactant can also be used without a stabilizing agent.

Preferably, the at least one stabilizing agent is present in the solvent in a concentration of about 10 mg/ml to about 200 mg/ml, based on the solvent or the non-solvent.

Preferably, the at least one surfactant is present in a concentration of about 1 mg/ml to about 200 mg/ml, based on the solvent or the non-solvent.

Preferably, the volume ratio of the solvent and the non-solvent is between about 1:1 and about 1:10, more preferably between about 1:2 and about 1:5, more preferably between about 1:2 and about 1:4.

The nanoparticles formed as described above are then preferably further processed to the final pharmaceutical formulation. In case that the final pharmaceutical formulation is an aqueous preferably first organic solvents have to be removed according to set authority limits. This can be realized by using a diafiltration or lyophilization process. pH and osmolarity can be readily adjusted during the diafiltration process, accordingly. If a solid dosage form is targeted, the whole nanoparticle suspension is preferably further processed by a drying process (e.g. wet granulation or fluid bed granulation, spray drying). The obtained powder can be further processed by common pharmaceutical processes.

The present invention also relates to nanoparticles comprising tacrolimus, which are obtainable by the method described above.

The present invention further relates to nanoparticles as described or obtainable by the method described for use as a medicament.

The present invention further relates to nanoparticles as described or obtainable by the method described for use in the prophylaxis and/or treatment of solid organ transplant rejection.

The present invention further relates to nanoparticles as described or obtainable by the method described for use as a medicament for treating pediatric patients.

The present invention further relates to nanoparticles as described or obtainable by the method described for use in the prophylaxis and/or treatment of solid organ transplant rejection in pediatric patients.

As "pediatric patients", children of the age up to about 18 years, preferably of 28 days to 17 years shall be understood.

The present invention further relates to the buccal administration of the nanoparticles as described or obtainable by the method described.

The present invention further relates to a mucoadhesive buccal film comprising at least one matrix layer containing nanoparticles containing tacrolimus as described or obtained by the method described.

Mucoadhesive buccal films are thin films containing at least one pharmaceutically active substance which are placed directly in the oral cavity or applied to the oral mucosa and dissolve there. In particular, these are thin polymer-based films containing active ingredients which, when applied to a mucous membrane, especially the oral mucosa, release the active ingredient directly into it. The active ingredient can be dissolved, emulsified or dispersed in the film. The very good blood circulation of the oral mucosa ensures a rapid transfer of the active substance into the blood circulation.

This delivery system has the advantage that the active ingredient is largely absorbed through the mucous membrane and thus the "first-pass metabolism", which occurs in the conventional delivery form of an active ingredient in tablet form, is avoided. Further, such a mucoadhesive buccal film has the advantage that tacrolimus is protected from degradation due to pH and digestive enzymes of the gastrointestinal tract. The mucoadhesive buccal film further provides a rapid onset of action relative to the oral route. The mucoadhesive buccal film is a particularly easy way of drug administration and therefore especially suitable for use in pediatrics. Moreover, such a mucoadhesive buccal film avoids hurdles related to drug administration via the nasogastric tube and is flexible in physical shape, state, size and surface. Moreover the mucoadhesive buccal film allows an accurate dosing as well as offering the possibility of masking the taste of tacrolimus.

In a preferred embodiment, the mucoadhesive buccal film according to the present invention is characterized in that the at least one polymer comprises a water-soluble and/or water-swellable polymer.

Water soluble/water swellable polymers comprise chemically very different natural or synthetic polymers whose common feature is their solubility/swellability in water or aqueous media. A prerequisite is that these polymers have a sufficient number of hydrophilic groups for water solubility/water swellability and are not cross-linked. The hydrophilic groups may be non-ionic, anionic, cationic and/or zwitterionic.

Preferably the at least one polymer in the mucoadhesive buccal film according to the present invention is selected from the group consisting of hydroxypropylmethyl cellulose, hydroxypropyl cellulose, hydroxyethyl cellulose, pea starch, pullulan, poly(meth)acrylate, e.g. known by the tradename Eudragit (Evonik), polyvinyl caprolactam-polyvinyl acetate-polyethylene glycol graft copolymer, e.g. known by the tradename Soluplus (BASF), chitosan, gummi *arabicum*, dextran, dextrin, alginate, polyvinylalcohol, polyvinylpyrrolidone and/or vinylpyrrolidon-vinylacetate-copolymer.

These polymers have the advantage that when dried they form a thin, stable film that dissolves or swells when applied to the mucous membrane within a pharmaceutically acceptable time and thus releases tacrolimus in the mucosa. This has the advantage of relatively rapid availability of the active ingredient as well as a preferably residue-free administration of tacrolimus.

In a preferred embodiment, the mucoadhesive buccal film according to the present invention is characterized in that the at least one polymer is contained in the mucoadhesive buccal film in an amount of about 10 to about 99.9% by weight, based on the total weight of the mucoadhesive buccal film.

In another preferred embodiment, the mucoadhesive buccal film according to the invention is characterized in that the nanoparticles comprising tacrolimus are contained in the mucoadhesive buccal film in an amount of about 0.1 to about 20% by weight, based on the total weight of the mucoadhesive buccal film.

The mucoadhesive buccal film according to the present invention is further preferably characterized in that the mucoadhesive buccal film comprises at least one adjuvant selected from the group comprising dyes, fillers, disintegrants, flavors, sweeteners, taste masking agents, emulsifiers, enhancers, pH regulators, humectants, preservatives and/or antioxidants.

Each of these adjuvants is preferably contained in the mucoadhesive buccal film in an amount of about 0.01 to about 10% by weight, based on the total weight of the mucoadhesive buccal film.

The mucoadhesive buccal film according to the present invention is further preferably characterized in that the basis weight of the mucoadhesive buccal film is about 20 to about 300 $g/m^2$, preferably about 50 to about 200 $g/m^2$.

This preferably corresponds to a layer thickness of about 20 m to about 500 m, preferably of about 50 m to about 300 m.

The mucoadhesive buccal film according to the present invention is preferably designed to achieve a daily dose of delivered tacrolimus in the range of about 0.2 mg to about 18 mg, and preferably of about 0.3 mg to about 18 mg. Of course the daily dose depends on the weight of the patient. Preferably the daily dose is about 0.2 to about 0.4 mg per kg, more preferably about 0.3 mg per kg. For this purpose, the mucoadhesive buccal film is provided in a suitable size, e.g. in the range from about 2 $cm^2$ to about 6 $cm^2$.

The mucoadhesive buccal film according to the present invention might contain at least one further layer on one side of the matrix layer, which comprises the same or a different polymer.

The at least one additional layer might also serve for stabilization of the mucoadhesive buccal film.

The at least one additional layer can be glued, using pharmaceutically acceptable adhesives, or hot-sealed onto the matrix layer.

Preferably, the further layer is a backing layer, which is preferably impermeable for tacrolimus. Thus, the mucoadhesive buccal film according to the present invention preferably comprises one backing layer, which is preferably impermeable for tacrolimus on one side of the at least one matrix layer.

In a further embodiment, the mucoadhesive buccal film according to the present invention is arranged on a removable carrier foil, which can be made of polyethylene paper, polypropylene or polyethylene terephthalate foil. The carrier foil is removed before application of the mucoadhesive buccal film The present invention further relates to the mucoadhesive buccal film described for use as a medicament.

The present invention further relates to the mucoadhesive buccal film as described for use in the prophylaxis and/or treatment of solid organ transplant rejection.

The present invention further relates to the mucoadhesive buccal film as described for use as a medicament for treating pediatric patients.

The present invention further relates to the mucoadhesive buccal film as described for use in the prophylaxis and/or treatment of solid organ transplant rejection in pediatric patients.

What is claimed is:

1. A method for producing nanoparticles containing tacrolimus or a salt thereof, the method comprising steps of:
    a) providing a solution of tacrolimus or a salt thereof in an organic solvent;
    b) providing a liquid non-solvent for the tacrolimus or the salt thereof;
    c) precipitating nanoparticles containing the tacrolimus or the salt thereof by colliding a stream of the organic solvent from step a) with a stream of the non-solvent from step b); and
    d) isolating the nanoparticles, wherein the nanoparticles have a size of from 10 nm to 400 nm, and a polydispersity index of less than or equal to about 0.4.

2. The method according to claim 1, wherein the solvent further comprises ethanol, methanol, acetone, and/or tetrahydrofuran.

3. The method according to claim 1, wherein the non-solvent comprises water.

4. The method according to claim 1, wherein the solvent and/or the non-solvent further comprises at least one stabilizing agent including polyvinyl pyrrolidone, vinylpyrrolidone-/vinylacetate-copolymer, polyethylenglycol and/or a cellulose derivative.

5. The method according to claim 1, wherein the non-solvent further comprises a non-ionic surfactant and/or an ionic surfactant.

6. The method according to claim 1, wherein the stream of the organic solvent from step a) and the stream of the non-solvent from step b) are collided with a velocity of about 1 m/sec to about 100 m/sec.

7. The method according to claim 1, wherein the stream of the organic solvent from step a) and the stream of the non-solvent from step b) are collided with a velocity of about 50 m/sec.

8. The method according to claim 1, wherein a volume ratio of the solvent and the non-solvent is between about 1:1 and about 1:5.

9. The method according to claim 4, wherein the cellulose derivative is selected from hydroxypropylmethyl cellulose (HPMC), hydroxypropylmethyl cellulose phthalate (HPMCP), hydroxypropylmethyl cellulose acetate succinate (HPMCAS), hydroxypropyl cellulose (HPC), and/or carboxymethyl cellulose (CMC).

* * * * *